US009809800B2

(12) United States Patent
Yanagida

(10) Patent No.: US 9,809,800 B2
(45) Date of Patent: Nov. 7, 2017

(54) METHOD FOR PRODUCING PARVOVIRUS HAVING HIGH INFECTIVITY TITER

(71) Applicant: ASAHI KASEI MEDICAL CO., LTD., Tokyo (JP)

(72) Inventor: Koichiro Yanagida, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/646,115

(22) PCT Filed: Sep. 5, 2013

(86) PCT No.: PCT/JP2013/073906
§ 371 (c)(1),
(2) Date: May 20, 2015

(87) PCT Pub. No.: WO2014/080676
PCT Pub. Date: May 30, 2014

(65) Prior Publication Data
US 2015/0299668 A1 Oct. 22, 2015

(30) Foreign Application Priority Data
Nov. 22, 2012 (JP) ................. 2012-256801

(51) Int. Cl.
C12N 5/10 (2006.01)
C12N 7/00 (2006.01)

(52) U.S. Cl.
CPC ...... C12N 7/00 (2013.01); C12N 2750/14351 (2013.01)

(58) Field of Classification Search
CPC .......... A61K 47/48676; A61K 51/1051; A61K 39/23; A61K 35/768; A61K 39/00; A61K 39/12; A61K 48/00; A61K 2039/5256; A61K 2039/552; A61K 2039/5252; A61K 2039/5254; C12N 2720/12351; C12N 2770/20051; C12N 2770/24051; C12N 2770/24151; C12N 2750/14351; C12N 15/85; C12N 2750/14311; C12N 15/86; C12N 2770/10051; C12N 2770/10064; G01N 2333/015; Y10T 436/143333; C07K 14/005; C07K 16/081; C07K 14/015
See application file for complete search history.

(56) References Cited

U.S. PATENT DOCUMENTS

| 4,870,023 | A | 9/1989 | Fraser et al. | |
|---|---|---|---|---|
| 4,904,468 | A | 2/1990 | Gill et al. | |
| 5,814,510 | A | 9/1998 | Parrish et al. | |
| 7,179,456 | B2 * | 2/2007 | Rommelaere | A61K 35/768 424/93.1 |
| 2009/0098159 | A1 | 4/2009 | Mochizuki | |

| 2010/0062489 | A1 | 3/2010 | Guehenneux et al. |
|---|---|---|---|
| 2010/0098725 | A1 | 4/2010 | Liu et al. |
| 2012/0088228 | A1 | 4/2012 | Asher et al. |
| 2013/0195913 | A1 | 8/2013 | Spibey |

FOREIGN PATENT DOCUMENTS

| JP | 58-22008 | 5/1983 |
|---|---|---|
| JP | 61-024370 | 2/1986 |
| JP | 2-502876 | 9/1990 |
| JP | 2655876 | 5/1997 |
| JP | 10-508485 | 8/1998 |
| JP | 99/47645 | 9/1999 |
| JP | 2001-527422 | 12/2001 |
| JP | 2009-297036 | 12/2009 |
| JP | 2010-524482 | 7/2010 |
| JP | 2012-503486 | 2/2012 |
| VU | 99/07834 | 2/1999 |
| WO | 99/07834 | 2/1999 |
| WO | 99/47645 | 9/1999 |
| WO | 2007/125605 | 11/2007 |
| WO | 2011/130119 | 10/2011 |
| WO | 2012/007589 | 1/2012 |

OTHER PUBLICATIONS

Iwata et al. Biol Pharm. Bull. 2003, vol. 26 (8). pp. 1065-1069.*
Paglino et al., "LuIII Parvovirus Selectively and Efficiently Targets, Replicates in, and Kills Human Glioma Cells", *Journal of Virology*, vol. 86, No. 13, pp. 7280-7291, 2012.
Slocum et al., "Impact of virus preparation quality on parvovirus filter performance", *Biotechnology and Bioengineering*, vol. 110, No. 1, pp. 229-239, published online Aug. 6, 2012.
Supplementary European Search Report issued in EP Patent Appl. No. 13856565.0, dated Sep. 30, 2015.
Bachmann et al., "Porcine Parvovirus Infection in vitro: A Study Model for the Replication of Parvoviruses", *Zbl. Vet. Med. B*, No. 23, pp. 355-363, 1976.
*Uirusu/Kansen new Fairu (Virus/Infection New File)*, edited by Yoshiyuki Nagai and Haruo Watanabe, Yodosha Co., Ltd, pp. 68, 1997.

(Continued)

Primary Examiner — Bao Li
(74) Attorney, Agent, or Firm — Greenblum & Bernstein, P.L.C.

(57) ABSTRACT

A method for stably and easily producing a parvovirus having a high infectivity titer is provided. The problem is solved by a method for producing a parvovirus having an infectivity titer as high as $10^8$ $TCID_{50}$/mL or more in a culture supernatant, comprising the steps of inoculating a seed virus of the parvovirus into a culture substrate comprising host cells having a cell density of 1/500 to 1/20 of the cell density of the host cells confluently grown and a medium at a multiplicity of infection of 0.0001 to 0.1, culturing for a period of 5 to 11 times the doubling time of the host cells, and recovering a culture supernatant.

15 Claims, No Drawings

(56) References Cited

OTHER PUBLICATIONS

*Uirusu Jikken Gaku Kakuron (Particular Experimental Virology)*, edited by Researcher's Associates, the National Institute of Health (Japan), pp. 22-23, 1973, along with a partial English language translation.

*Uirusu-gaku (Virology)*, edited by Masakazu Hatanaka, Asakura Publishing Co., Ltd., pp. 222-223, 1997.

Gregersen, "Herstellung von Virusimpfstoffen aus Zellkulturen", *Pharmazeutische Biotechnologie*, edited by Kayser and Muller, pp. 257-281, 2000.

Bachmann, "Porcine Parvovirus Infection In Vitro: A Study Model for the Replication of Parvoviruses", *Proc. Soc. Exp. Biol. Med.*, vol. 140. No. 4, pp. 1369-1374, 1972.

Bachmann et al., "Porcine Parvovirus Infection in vitro: A Study Model for the Replication of Parvoviruses", *ZbL Vet. Med. B*, No. 23, pp. 355-363, 1976.

*Uirusu Jikken Gaku Sohron (General Experimental Virology)*, edited by Researcher's Associates, the National Institute of Health (Japan), pp. 61-180, 1973, along with a partial English language translation.

Azetaka et al., "Studies on Canine Parvovirus Isolation, Experimental Infection and Serologic Survey", *Jpn. J. Vet. Sci.*, vol. 43, pp. 243-255, 1981.

International Search Report from PCT/JP2013/073906, dated Nov. 19, 2013, along with an English language translation.

International Preliminary Report on Patentability from PCT/JP2013/073906, dated May 26, 2015, along with an English language translation.

* cited by examiner

METHOD FOR PRODUCING PARVOVIRUS HAVING HIGH INFECTIVITY TITER

TECHNICAL FIELD

The present invention relates to a method for producing a parvovirus having a high infectivity titer in a culture supernatant, and a parvovirus solution having a high infectivity titer obtained by the method.

BACKGROUND ART

Viruses infect plants and animals including humans and microbes and amplify. Some are DNA viruses having DNA as a genome and others are RNA viruses having RNA as a genome; these viruses have different amplification mechanisms. Many viruses cause viral infection when infecting animals including humans. Viruses cannot increase by themselves, and can increase by infecting cells of other animals/plants/microbes and using the capability of the cells. Cells that a virus can infect for growth are called "host cells" for the virus. The type of host cells that a virus can infect for growth is dependent on the type of the virus.

Parvovirus is a small single-stranded DNA virus, and is an envelope-free icoshedral virus having a diameter as small as about 20 nm (Non Patent Literature 1). Parvovirus infects animals to cause a disease. Known examples of the disease include anemia due to simian parvovirus (SPV), cat enteritis/leucopenia/dystonia due to feline parvovirus (FPV), dog enteritis/myocarditis due to canine parvovirus (CPV), pig stillbirth due to porcine parvovirus (PPV), cow enteritis due to bovine parvovirus (BPV), goose enteritis/myocarditis due to goose parvovirus (GPV), and mouse enteritis/hepatitis due to minute virus of mice (MVM) in addition to infectious erythema, anemia, and arthritis that B19 parvovirus causes in humans (Non Patent Literatures 2 and 3). Parvovirus is important as a pathogen causing diseases in animals kept by humans, such as dogs and cats. When dogs are infected with canine parvovirus, they are known to experience enteritis as described above, develop severe diarrhea and vomiting, and die (Non Patent Literature 3). When cats are infected with parvovirus, they sometimes develop acute enteritis or leukopenia and also have the possibility of dying from a secondary infection, and when fetuses or newborn infants are infected with the virus, they may be damaged in the central nerve and the thymus to develop ataxia or die.

To prevent parvovirus infection, vaccines against parvovirus have been studied (Patent Literatures 1 and 2). To perform these studies, it is necessary to produce the virus for use. Many viruses can be grown and produced by culturing host cells and infecting the cells with the viruses. The production of a vaccine whose virus is attenuated or inactivated is achieved by the same procedure as that for virus production.

In the pharmaceutical industry, it is necessary to evaluate virus clearance (removal performance) of the production steps in order to assure no contamination of a pharmaceutical product of biological origin, such as a recombinant pharmaceutical product (a biopharmaceutical product) or an antibody pharmaceutical product, with virus (virus safety). Hence, the virus clearance of the individual step is measured by adding the virus to an intermediate pharmaceutical product before each step and quantitating the amount of the virus before and after the step. Particularly, porcine parvovirus (PPV) as one type of parvovirus is used at a high frequency in the virus clearance evaluation of a plasma derivative performed by the method described in the ICH (International Conference on Harmonisation of Technical Requirements for Registration of Pharmaceuticals for Human Use) guideline prescribed for the method of selecting the type of the virus used for the virus clearance evaluation of the producing steps of a biologics, and minute virus of mice (MVM) as a type of parvovirus is used at a high frequency in the virus clearance evaluation of a biopharmaceutical product. Thus, parvovirus is used at a high frequency for the virus clearance evaluation of the producing steps of a biologics.

There are a method using a laboratory animal, a method using hen's eggs, and a method using tissue culture/cultured cells to produce a virus (Non Patent Literature 4). The methods using a laboratory animal and hen's eggs have the disadvantage of high cost. The alternate method is a method using cultured cells (Non Patent Literature 5). Parvovirus is also produced by a method using cultured cells (Patent Literature 1).

To produce a virus such as parvovirus, a method is commonly performed which involves infecting a culture system of host cells with its seed virus and growing and recovering the virus. As used herein, the seed virus is referred to a small amount of the virus used at the beginning of virus growth deemed as "seed". In conventional virus production, the timing at which host cells are infected with the seed virus is typically a stage at which the host cells have reached confluence to form a single layer state (Non Patent Literature 4 and Patent Literatures 3 to 6). In other words, typically, host cells are inoculated in a culture vessel and grown so that the host cells spread by growth on the full area of the bottom face of the culture vessel and then, a seed virus is inoculated; this is because when infectable cells are present at higher density, a system for a place in which more particles of the virus are produced is provided. Two to three days are typically required from the inoculation of the host cells in the culture vessel until their reaching a confluent state (Non Patent Literature 4). In the confluent state, the host cells are in a stationary phase and do not further grow. Thus, the conventional technology involves completing a growing culture step for host cells, starting virus infection in a culture environment in which the cells are not further grown, and producing the virus in the culture supernatant in parallel with the death of the host cells from the virus infection. Parvovirus is no exception in such a method; the virus was produced by a method involving infecting cells in a state of confluence (Non Patent Literatures 6 and 7) and the infectivity titer of the resultant parvovirus was $10^5$ to $10^7$ $TCID_{50}$/mL. In the conventional culture system, parvovirus is added to host cells in a confluent state in which the number of cells is highest, and the added parvovirus grows in host cells and increases with the attendant death of the host cells. A culture supernatant can be recovered at a stage when the infectivity titer of parvovirus becomes highest to recover a parvovirus solution having a highest infectivity titer. The parvovirus obtained in the culture supernatant by this method is naturally recovered in a state suspended in the medium provided for the cell culture.

The removal of impurities is also performed for the parvovirus solution obtained as described above. The removal of impurities, such as cell debris, by low-speed centrifugation is carried out as the removing method. As methods for removing more impurities, there are also known cesium chloride density-gradient ultracentrifugation using an ultracentrifugation technique and a sucrose density-gradient ultracentrifugation technique (Non Patent Literature 8).

CITATION LIST

Patent Literature

Patent Literature 1: WO2007/125605
Patent Literature 2: National Publication of International Patent Application No. 1998-508485
Patent Literature 3: Japanese Patent Laid-Open No. 2009-297036
Patent Literature 4: Japanese Patent No. 2655876
Patent Literature 5: Japanese Patent Laid Open No. 58-22008
Patent Literature 6: Japanese Patent Laid-Open No. 61-24370

Non Patent Literature

Non Patent Literature 1: Uirusu/Kansen new Fairu (Virus/Infection New File) 1997, edited by Yoshiyuki Nagai and Haruo Watanabe, Yodosha Co., Ltd., p. 68
Non Patent Literature 2: Uirusu-gaku (Virology) 1997, edited by Masakazu Hatanaka, Asakura Publishing Co., Ltd., p. 222-223
Non Patent Literature 3: M. Azetaka et. al 1980, Jpn. J. Vet. Sci. 43: 243-255
Non Patent Literature 4: Uirus Jikken Gaku Sohron (General Experimental Virology) edited by Researcher's Associates, the National Institute of Health (Japan), 1973, p. 61-180
Non Patent Literature 5: Gregersen, J. P. Pharmazeutische Biotechnologie, edited by Kayser and Muller, 2000, p. 257-281
Non Patent Literature 6: P. A. Bachmann 1972, Proc. Soc. Exp. Biol. Med. (140) 4: 1369-1374
Non Patent Literature 7: P. A. Bachmann et al. 1976, Zbl. Vet. Med. B., No. 23: 355-363
Non Patent Literature 8: Uirus Jikken Gaku Kakuron (Particular Experimental Virology), 1973, edited by Researcher's Associates, the National Institute of Health (Japan), p. 22-23

SUMMARY OF INVENTION

Technical Problem

As described above, there is a need for the production of a parvovirus having a high infectivity titer for use in the virus safety evaluation of a pharmaceutical product of biological origin and the production of a vaccine against the virus.

There is also a need for the production of a virus having a high infectivity titer in the virus clearance evaluation of the production steps of a biologics described above. The virus clearance test of a virus removal filter for the evaluation is performed in a model steps in which the actual production steps are scaled down; the required points for the virus clearance test are, firstly, that the addition amount of a virus suspension is an amount to an extent not clogging the holes of the filter, and secondly, that the addition amount is an amount capable of ensuring that the log reduction value (LRV) as a virus clearance value for a step to be evaluated is 4 or more. For the former, the addition amount needs to be set to an amount not causing clogging due to virus addition because parameters including the flow rate in the step must be the same as those in the actual production steps (WHO Technical Report, Series No. 924, 2004 162-165). For that purpose, it is desirable to add the suspension in a volume ratio of 1% or less, preferably 0.1% or less. For the latter, the virus addition amount needs to be set to an amount capable of resulting in LRV being 4 or more since the step having an LRV of 4 or more is regarded as a robust, effective, and reliable step in virus removal (WHO Technical Report, Series No. 924, 2004 163-164). Thus, LRV as a virus removal performance needs to be ensured to be 4 or more, and the amount of the virus suspension added to an intermediate product is desirably 1% or less, preferably 0.1%, by volume. However, when 1% or 0.1% of a parvovirus having low infectivity titer obtained by a conventional culture method (infectivity titer: $10^5$ to $10^7$ $TCID_{50}$/mL, infectivity titer of parvovirus ($TCID_{50}$/mL):impurity protein concentration (ng/mL) ratio=less than 10:1) is added, it is difficult to result in an LRV of 4 or more, because of problems of loss in a prefilter and quantitative error. Here, to unfailingly obtain an LRV of 4 or more, the virus addition volume must be increased, which results in higher rate of the occurrence of negative effects, such as clogging the holes of the filter.

To solve these problems, a conventionally available method which involves precipitating and concentrating virus by ultracentrifugation, such as density gradient ultracentrifugation or sucrose density gradient ultracentrifugation. However, impurities are simultaneously concentrated, which has problems of producing detrimental effects of impurities on experimental results and filtration with a virus removal filter.

The use of ultracentrifugation, such as density gradient ultracentrifugation or sucrose density gradient ultracentrifugation, results in the separated and purified virus having extremely high purity and a virus infectivity titer ($TCID_{50}$/mL):impurity protein concentration (ng/mL) ratio will be 10,000 or more:1, and there will be a problem that virus particles easily aggregate because of reduced impurities. In the virus clearance evaluation of the production steps of a biologics, if virus particles aggregate, there is a problem that the virus clearance is overestimated because the virus is separated and removed even with a filter having such a pore diameter that the virus passes in nature.

In addition, the technique of ultracentrifugation, such as cesium density gradient ultracentrifugation or sucrose density gradient ultracentrifugation, is cumbersome in operation and requires a difficult technical skill. Further, the technique can generally be used only in a small-scale experiment because the volume of a centrifuge tube in a general purpose ultracentrifuge is limited, making scale-up difficult; thus, the industrial adoption of these purification steps is not practical.

To obtain a virus suspension having a high infectivity titer, a method is also known which involves recovering infected cells, forcibly/physically destructing the cells by a repetition of freezing and thawing, and recovering the virus accumulated in the cells. This method is a virus production method commonly performed for minute virus of mice and the like; however, this method results in contamination of the suspension with a large amount of impurities from the interior of host cells and thus, even though the virus is obtained at a high infectivity titer, the impurity concentration is relatively increased. Thus, the method results in the necessity of a cumbersome operation, such as ultracentrifugal purification, in using the virus, and has the same problem as above.

As described above, it is extremely difficult to adopt the conventional virus production techniques, and there is a need for a method for more simply and efficiently obtaining a parvovirus solution having appropriate purity and a high infectivity titer, without using a complicate operation, such as ultracentrifugal separation.

Solution to Problem

To solve the above problems, the present inventors have intensively studied the relation between various conditions (initial host cell density and multiplicity of infection (MOI)) upon growing the parvovirus in a culture system and the infectivity titer of the virus, by culturing the host cells for a parvovirus and inoculating a seed virus of the parvovirus thereinto. As a result, it has surprisingly been found that, using a growth mechanism typical of the parvovirus, a parvovirus solution having an extremely high infectivity titer, not obtained by conventional methods are obtained by infecting host cells having an extremely low cell density within a specific range not previously adopted, with a seed virus of the parvovirus at a specific range of low MOI, culturing the host cells for a specified period, and recovering a culture supernatant.

Thus, the present invention is as follows.

[1]

A method for producing a parvovirus having an infectivity titer as high as $10^8$ $TCID_{50}$/mL or more in a culture supernatant by culturing host cells and a seed virus of the parvovirus in a culture substrate, comprising the steps of:

(a) previously calculating a doubling time of the host cells during the log growth phase in the culturing and a cell density of the host cells confluently grown in the culturing;

(b) inoculating the seed virus of the parvovirus into the culture substrate comprising the host cells having a cell density of 1/500 to 1/20 of the cell density of the host cells confluently previously grown calculated in the step (a) and a medium to give a multiplicity of infection (MOI) of 0.0001 to 0.1;

(c) culturing a culture comprising the host cells and the parvovirus of the step (b) for a period of 5 to 11 times the doubling time previously calculated in the step (a); and (d) recovering a culture supernatant comprising the parvovirus, obtained by the culturing step (c).

[2]

The method according to [1], wherein the host cell is an adhesion-dependent cell.

[3]

The method according to [1] or [2], wherein the host cell is a cell susceptible to the parvovirus.

[4]

The method according to any of [1] to [3], wherein the parvovirus is porcine parvovirus (PPV), canine parvovirus (CPV), minute virus of mice (MVM), rat virus (RV), H-1 virus (H-1), feline parvovirus (FPV), goose parvovirus (GPV), or bovine parvovirus (BPV).

[5]

The method according to any of [1] to [4], wherein in the step (b), the seed virus of the parvovirus is inoculated into the culture substrate comprising the host cells having a cell density of 1/300 to 1/30 of the cell density of the host cells confluently grown previously calculated in the step (a) and a medium to give a multiplicity of infection (MCI) of 0.0001 to 0.1.

[6]

The method according to any of [1] to [4], wherein in the step (b), the seed virus of the parvovirus is inoculated into the culture substrate comprising the host cells having a cell density of 1/200 to 1/40 of the cell density of the host cells confluently grown previously calculated in the step (a) and a medium to give a multiplicity of infection (MCI) of 0.0001 to 0.1.

[7]

The method according to any of [1] to [6], wherein the multiplicity of infection (MCI) is 0.001 to 0.03.

[8]

The method according to [7], wherein the multiplicity of infection (MCI) is 0.003 to 0.01.

[9]

The method according to any of [1] to [8], wherein when the medium is a serum medium, the step (c) comprises a step of replacing the serum medium with a serum-free medium.

[10]

The method for producing a parvovirus according to any of [1] to [9], wherein in the step (c), the culture is cultured for a period of 6 to 9 times the doubling time previously calculated in the step (a).

[11]

The method for producing a parvovirus according to [10], wherein in the step (c), the culture is cultured for a period of 7 to 8 times the doubling time previously calculated in the step (a).

[12]

The method for producing a parvovirus according to any of [1] to [11], wherein in the step (c), the culture is cultured at a temperature of 33° C. or higher and 39° C. or lower.

[13]

The method for producing a parvovirus according to any of [1] to [12], wherein in the step (c), the host cells and the virus grow concurrently.

[14]

The method according to any of [1] to [13], wherein the step (d) comprises a step of removing free host cells and host cell debris contained in the culture supernatant.

[15]

The method according to [14], wherein the removing step is performed using filtration with a membrane having a pore diameter of 0.2 μm to 0.45 μm.

[16]

A culture solution comprising the parvovirus having an infectivity titer of $10^8$ $TCID_{50}$/mL or more, obtained by the method according to any of [1] to [15].

[17]

A parvovirus solution obtained by cell culturing, comprising a parvovirus having an infectivity titer of $10^8$ $TCID_{50}$/mL or more, wherein a ratio of the infectivity titer ($TCID_{50}$/mL) of the parvovirus to a concentration (ng/mL) of impurity proteins is 10:1 to 5,000:1.

Advantageous Effect of Invention

The present invention can simply and efficiently provide a parvovirus solution having an infectivity titer as high as $10^8$ $TCID_{50}$/mL or more by cell culture, and overcomes negative effects due to an insufficient infectivity titer in using parvovirus.

DESCRIPTION OF EMBODIMENTS

An embodiment of the present invention (hereinafter referred to as "the present embodiment") will be described below in detail. However, the present invention is not intended to be limited to the following present embodiment, and various modifications can be made within the scope of the gist of the invention.

The present embodiment is a method for producing a parvovirus having an infectivity titer as high as $10^8$ $TCID_{50}$/ mL or more in a culture supernatant by culturing host cells and a seed virus of the parvovirus in a culture substrate, comprising the steps of:

(a) previously calculating a doubling time of the host cells during the log growth phase in the culturing and a cell density of the host cells confluently grown in the culturing;

(b) inoculating the seed virus of the parvovirus into the culture substrate comprising the host cells having a cell density of 1/500 to 1/20 of the cell density of the host cells confluently grown previously calculated in the step (a) and a medium to give a multiplicity of infection (MCI) of 0.0001 to 0.1;

(c) culturing a culture comprising the host cells and the parvovirus of the step (b) for a period of 5 to 11 times the doubling time previously calculated in the step (a); and (d) recovering a culture supernatant comprising the parvovirus, obtained by the culturing step (c).

Step (a): A doubling time of the host cells for the parvovirus during the log growth phase and a cell density of the host cells confluently grown are previously calculated. The host cells may be grown by passage culture.

Parvovirus is a small linear single-stranded DNA virus. A DNA virus is a virus having DNA as a genome, synthesizes mRNA from the genome DNA by using the RNA polymerase of a host cell, and grows by synthesizing proteins based on the mRNA. Most DNA viruses are double-stranded DNA viruses, but parvovirus has linear single-stranded DNA as a genome. A virus cannot grow in a state of single-stranded DNA; thus, parvovirus has a unique growth mechanism in which the virus grows via a state of double-stranded DNA by using DNA polymerase in addition to the RNA polymerase of a host cell.

The Parvoviridae virus family is known to comprise 3 genera belonging to Parvorivinae: the genus Parvorivirus, which does not require a helper virus for virus replication and autonomously grows in a host cell; the genus Dependovirus, which requires the helper virus; and the genus Erythrovirus, which specifically infects erythrocytes, and 3 genera belonging to Densovirinae: the genus Densovirus which infects insects, the genus Iteravirus, and the genus *Aedes aegypti* densovirus. In the present embodiment, the "parvovirus" refers to a virus of the genus Parvorivirus. Viruses of the genus Parvorivirus have similar growth mechanisms and thus can be used in common by the method of the present embodiment.

In the present embodiment, the parvovirus (virus of the genus Parvorivirus) encompasses, but not limited to, porcine parvovirus (PPV), canine parvovirus (CPV), minute virus of mice (MVM), rat virus (RV), H-1 virus (H-1), feline parvovirus (FPV), goose parvovirus (GPV), and bovine parvovirus (BPV). These viruses are similar in size, genome structure, virus particle structure, and growth mechanism, and all of the viruses can be suitably used in the method of the present embodiment.

According to the present embodiment, the "host cell" may be any type of cell provided that it is a cell susceptible to a parvovirus (can be infected with the parvovirus). Examples of the cell susceptible to a parvovirus include PK-13 cells, PK-15 cells, LCC-PK1 cells, ESK (embryonic swine kidney) cell, SK cells, ST (swine testes) cells, and MPK (minipig kidney) cells which are all susceptible to porcine parvovirus; MDCK (Mardin-Darby canine kidney) cells, FEA (feline embryonic fibroblast) cells, CRFK (Crandell feline kidney) cells, and FK-81 (embryonic feline kidney) cells which are all susceptible to canine parvovirus; A9 (mouse fibroblast) cells and C6 (rat glial) cells which are all susceptible to minute virus of mice; NRK (normal rat kidney) cells susceptible to rat virus; Molt-4 cells (human T-cells), AV-1 cells (human B-cells), and NC-37 cells (human B-cells) which are all susceptible to H-1 virus; CRFK cells, Mya 1 cells, NLFK (Norden Laboratories feline kidney) cells, and A72 cells which are all susceptible to feline parvovirus; GEF (goose embryo fibroblast) cells susceptible to goose parvovirus; and BEK (bovine embryonic kidney) cells, buffalo lung fibroblast cells, and EBTr (bovine embryonic trachea) cells which are all susceptible to bovine parvovirus. The host cell is preferably a cell producing cellular degeneration by infection. By way of non-limiting example, the host cells may be porcine kidney cells for porcine parvovirus and canine kidney cells for canine parvovirus; as described above, the host cells can be widely used provided that they are cells susceptible to parvovirus and preferably producing cellular degeneration. According to the present embodiment, the "host cells" may be animal cells having infinite proliferative capacity, and may be those generally called "cell line".

According to the present embodiment, the host cells are preferably adhesion-dependent cells. The "adhesion-dependent cells" are cells capable of surviving/growing only in a state adhering to a culture substratum such as muscle cells and organ cells. The adhesion-dependent cells are cultured by adhesion to the bottom face/wall face of a culture substrate, such as a culture flask, or a carrier called a microcarrier. A flask and a petri dish are commonly used for small-scale culture. The culture using microcarriers has an advantage of being easily scaled up successively (Japanese Patent No. 3982843, Method for Successively Culturing Animal Cells Using Porous Carrier). According to the present embodiment, floating cells can also be used. The "floating cells" grow in a floating state and are cultured by standing culture or stirred culture in a suspended state in a medium. For floating cells, because it is difficult to replace the medium before recovering a culture supernatant, for example, the cells are desirably cultured by adhering to microcarriers.

According to the present embodiment, the type of "culture substrate" is not intended to be limited and encompasses any culture substrate commonly used for cell culture, such as a culture vessel, a culture flask, a petri dish, a roller bottle, or a culture plate.

The culture suitably uses Dulbecco's Modified Eagle medium (DMEM medium), and can be performed under an environment of about 5% carbon dioxide gas; however, the conditions of the culture are not intended to be limited thereto provided that they are environmental culture conditions suitable for the growth of host cells. The culture temperature may be a temperature suitable for the growth of host cells. Host cells for parvovirus are known to grow in a range of 33° C. to 39° C. ("*Dobutsu Saibo Baiyoho Nyumon* (Introduction to Animal Cell Culture), (*Seibutsukagaku Jikkenho* 29 (Method of Biochemical Experiment 29)), Yutaka Matsutani/Gakkai Shuppan Center" p. 14-15); thus, the culture temperature may be preferably 33° C. or higher and 39° C. or lower, for example, about 37° C. It is desirable to use a medium containing 10% or less of animal serum (fetal bovine serum, calf serum, horse serum, or the like) containing a cell growth factor. The use of a serum-free medium reduces the amount of production of the virus; thus, it is also possible to replace the medium with the serum-free medium before virus recovery, and after a necessary and sufficient amount of cells have been grown in the serum medium.

According to the present embodiment, the "infectivity titer" is a unit denoting the infectious titer of a virus. It has the same meaning as "titer" often used in the virus field. A virus cannot be seen even by using an optical microscope and thus, unlike biological cells, density (the number of virus particles per volume) of the virus cannot be measured under the microscope. Thus, for a virus, the unit of the infectious titer utilizing the ability to infect host cells is used as an alternative to the amount and concentration of the virus. For example, when a virus suspension diluted at a suitable degree is added to a single layer of host cells, the number of virus particles can be detected as plaques to measure the infectious titer in plaque forming units (pfu)/mL. Alternatively, a virus-containing fluid is progressively diluted, and the concentration at which infection is positive in 50% of host cells can be defined as 50% tissue culture infectious dose ($TCID_{50}$)/mL to measure the infectious titer. According to the present embodiment, the infectious titer can be measured in $TCID_{50}$/mL for each of the parvoviruses used, and the infectious titter is indicated in $TCID_{50}$/mL. The infectious titer of a parvovirus may be represented in another unit such as pfu/mL. For the parvovirus capable of measuring the infectious titer using another unit, the same parvovirus suspension can be simultaneously measured for the infectious titer in both units to easily convert between the different units.

According to the present embodiment, the "doubling time during the log growth phase" is the amount of time required for host cells during the log growth phase to increase by 2-fold. The growth curve of cells shifts from the log growth phase to the stationary phase to the death phase. In the log growth phase, cells repeat cell division at a constant rate for growth. The doubling time varies depending on the type of cells, the medium conditions such as the serum concentration, and the culture conditions such as the culture temperature. The doubling time during the log growth phase can be calculated by the equation:

Doubling time (hour)=$0.301 t/\log 10[C2/C1]$ where t is the culture time; C1 is the initial number of cells; and C2 is the number of cells after culture.

When growth proceeds, the number of cells in the culture vessel soon reaches the upper limit. This is a stage in which growth stops due to the lack of nutrients, the accumulation of waste products, a decrease in pH value, and the like, and called the stationary phase. At this time, adhesion-dependent cells are in a dense state in which the adhesion-dependent cells completely cover the surface of the culture vessel, and the state is called "confluence". To determine the number of cells (density) when confluence is reached, cells may be recovered every 24 hours after inoculating the cells in the culture vessel to measure the number of the cells, thereby obtaining the number of the cells (density) when reaching the upper limit.

According to the present embodiment, the number of cells or the cell density when the host cells grow confluently is defined as follows. First, host cells are inoculated into a culture substrate, such as a culture flask, and then passage cultured, and the number of cells is measured every 24 hours to calculate the doubling time during each 24 hours. The measurement of the number of cells every 24 hours is ended on the next day of the day on which the doubling time is increased to 5 times or more the doubling time during the log growth phase; however, the measurement is also ended when the number of cells is decreased for 2 consecutive days.

Then, the average of data from the total 3 days consisting of the day at which the highest number of cells is reached and the days before and after that day is defined as the number of cells or the density of cells at confluence. Some types of cells take a long time to shift to the death phase after reaching the stationary phase and maintain the stationary phase for a long time. In this case, the day when the doubling time is increased to 5 times or more the doubling time during the log growth phase is used as the confluence achieving day, and the average of the numbers of cells at the achieving day and the day thereafter is defined as the number of cells or the density of cells at confluence. The number of cells every 24 hours is measured for separate culture substrates in all of which the culture has been simultaneously started under the same conditions, and cells are not returned to the culture substrate in which the number of cells has once been measured, for a repeated use for measurement at the day thereafter. The reason therefor is to avoid the influence of the lag time of growth due to the cell recovery operation. To eliminate measurement error and the error between each culture vessel whenever possible, at least 2 (n=2), preferably 3 (n=3), more preferably 4 (n=4) or more culture vessels are measured at a time. The number of cells and the density of cells at confluence vary depending on the culture conditions, such as the culture substrate, the medium, the type of cells, and the culture temperature. Thus, it is necessary to perform the measurement by the above method for each culture condition. After the stationary phase during which confluence is reached, the cells die from nutrient depletion and the like. This is called the death phase.

The "passage culture" is commonly carried out in a state of 60% to 80% confluence during the late log growth phase; when confluence is reached, growth stops for adhesion-dependent cells, and thus it is necessary to perform the passage culture before the confluence is reached (Hideki Koyama, *Saibo Baiyo Rabo Manyuaru* (Cell Culture Lab Manual) Springer-Verlag Tokyo 1999, p. 51-52). The repetition of the passage culture after confluence is reached weakens cells and may change their properties. Floating cells can be passaged by diluting the cells in fresh medium for subculture. Adhesion-dependent cells are passaged by detaching the host cells from the culture vessel with a proteinase such as trypsin, a chelating agent such as EDTA, or a mixture thereof, diluting the number of the cells, and subculturing the cells in a new culture vessel. The passage culture is commonly carried out twice to thrice a week by 2- to 12-fold dilution. For example, MDCK (canine kidney cells) as host cells for canine parvovirus are passaged by 2- to 6-fold dilution every 2 to 3 days (Toru Akiyama, *Saibo/Baichi Katsuyo Handobukku* (A Handbook for Practical Usage of Cell/Medium), Yodosha Co., Ltd, 2008, p. 45-46). Thus, in the passage culture of host cells for virus, the cells can be passaged by diluting the number of the cells to 1/2 to 1/12 of the number of the cells in confluence at a stage when the number of the cells has reached 60 to 80% of the number of the cells in confluence. In this range, considering a balance with the above passage frequency, the cell passage frequency and the dilution degree are suitably set for each cell. This is basically the same for floating cell culture.

Step (b): Then, a seed virus of the parvovirus is inoculated into a culture substrate containing host cells having a cell density of 1/500 to 1/20 of the cell density of the host cells confluently grown previously calculated in the step (a) and a medium to give a multiplicity of infection (MOI) of 0.0001 to 0.1.

As described above, it is necessary in the step (b) to prepare a culture substrate containing host cells having a cell density of 1/500 to 1/20 of the cell density of host cells confluently grown previously calculated in the step (a) and a medium. Here, the substrate is prepared by inoculating host cells having the above specified cell density in a culture substrate containing a medium, or culturing host cells in a culture substrate containing a medium to give the above specified cell density. The culture substrate preferably contains host cells having a cell density of 1/300 to 1/30, more preferably 1/200 to 1/40, of the cell density of the host cells confluently grown previously calculated in the step (a).

An important feature of the present embodiment is that infection is started at a predetermined cell density as extremely low as 1/500 to 1/20 of the cell density of host cells confluently grown as described above. For parvovirus, conventionally common method for producing the virus involves infecting host cells in a confluent state with a virus and in such method, host cells are not grown and only on the way to death via cell degeneration due to infection. On the other hand, host cell growth and virus growth have successfully been achieved concurrently by starting infection at an extremely low host cell density according to the present embodiment. Without being bound to theory, the concurrent occurrence of the host cell growth and the virus growth is probably attributed to the growth mechanism typical of a parvovirus. Specifically, a parvovirus is a DNA virus and transfers into the nuclei in host cells for DNA replication and thus, unlike other viruses capable of growing in the cytoplasm, the parvovirus grow slowly and does not rapidly kills infected cells, which probably allows the cell growth in the culture system as a whole. For the infection in a confluent state as a conventional technique, since host cells finish the log growth phase and reach a plateau, the growth of the parvovirus, even though being slow, has not been accompanied by cell growth. In contrast, according to the present embodiment, a parvovirus having a high infectivity titer can be provided by using the growth mechanism typical of the parvovirus to secure the sufficiently long "concurrent growth time of host cells and the virus" (hereinafter simply referred to as "concurrent growth time") during which the host cell and the virus grow concurrently. To secure the sufficiently long concurrent growth time, the seed virus is infected at a suitable host cell density. Too high a host cell density at infection makes it difficult to secure the sufficiently long concurrent growth time because the host cells reach confluence in a short period of time, resulting in stoppage of cell growth. Too low a cell density at infection also makes it difficult to secure the sufficiently long concurrent growth time because the parvovirus growth rate exceeds the host cell growth rate, resulting in the advancement of cell destruction. Thus, the present embodiment focuses not simply on the culture time of virus-infected host cells but on the above concurrent growth time. From such a viewpoint, the cell density of the host cells confluently grown is previously calculated and measured in the step (a), as previously described. Then, with the ratio to the cell density of the host cells confluently grown calculated in the step (a), the cell density of the host cells upon inoculating the seed virus of the parvovirus in the step (b) is specified.

In addition, according to the present embodiment, too short a concurrent growth time makes the amount of parvovirus growth insufficient and does not provide a parvovirus having a high infectivity titer, as described above. In contrast, without being bound by theory, a longer concurrent growth time than required causes the growth of a parvovirus to exceed the growth of host cells, renders all the host cells to proceed toward death, results in the inactivation of the parvovirus by the effect of protease released form the cells and the like, and decreases the infectivity titer. As the step (c) will be described below in detail, the culture can be recovered in suitable timed relation to keep the concurrent growth time in a suitable range to provide a parvovirus having an infectivity titer as extremely high as $10^8$ TCID$_{50}$/mL or more in a culture supernatant.

In the step (b), the seed virus of a parvovirus is inoculated into a culture substrate containing host cells having the specified low cell density and a medium to give a multiplicity of infection (MOI) of 0.0001 to 0.1. Here, the "multiplicity of infection" is the ratio of the virus addition amount to the number of host cells, and expressed by the virus infectivity titer/the number of the host cells. The inoculation of the seed virus of a parvovirus may be performed to give an MOI of 0.0001 to 0.1 simultaneously with the inoculation of host cells having the above predetermined cell density in a culture substrate. Alternatively, the culture of host cells may be started at a lower cell density, followed by inoculating the seed virus to give an MOI of 0.0001 to 0.1 at the time of achieving the predetermined cell density. The multiplicity of infection (MOI) of the parvovirus is preferably 0.001 to 0.03, more preferably 0.003 to 0.01.

When infection is started by inoculating host cells having the predetermined low cell density with the seed virus of a parvovirus to give a multiplicity of infection (MCI) of 0.0001 to 0.1, the parvovirus infection starts slowly, and the total number of the cells increases at first while the total amount of the parvovirus also increases; however, the growth rate of the parvovirus exceeds the growth rate of the host cells at some point of time, resulting the production of the virus at a high infectivity titer. The seed virus having infected the host cells replicates itself by the function of the host cells in the host cells and is extracellularly released or remains in the cells. In the cells infected with the virus, some virus cause cell degeneration and others do not. The virus causing cell degeneration has virulence; however, the virus not causing call degeneration has no virulence and causes persistent infection. The cell degeneration causes cell death. According to the present embodiment, preferred are, but not limited to, cells causing cell degeneration because of a larger amount of virus production.

Step (c): After inoculating the seed virus of a parvovirus, the culture containing the parvovirus and host cells is cultured for a predetermined period of time. In the step (c), the host cells and the parvovirus grow concurrently. The culture time is 5 to 11 times, preferably 6 to 9 times, more preferably 7 to 8 times, the doubling time of the host cells. When culture is carried out for the predetermined period of time, as described above, the host cells cause cell degeneration and die and a large amount of the parvovirus is released into a culture supernatant; thus, the culture supernatant is recovered at that stage to make the concurrent growth time in a suitable range to provide a parvovirus suspension having a high infectivity titer. The virus may also be released at a high infectivity titer into the culture supernatant without the death of almost all of the host cells; however, either mode of release will take place in the present embodiment. The culture temperature may be a temperature suitable for the growth of the host cells, and may be preferably 33° C. or higher and 39° C. or lower, for example, about 37° C. The culture is desirably carried out under the same conditions as the culture conditions of the step (a); thus, the culture temperature is desirably a temperature comparable to the culture temperature of the culturing in the step (a) when the doubling time of host cells during the log growth phase and the cell density of the host cells confluently grown are previously calculated.

When serum medium is used as a medium, the serum medium may be replaced with a serum-free medium immediately before or before the recovery of the culture supernatant in step (d) below, followed by further culturing in the serum-free medium to perform culture for the predetermined period of time as a whole. This enables the elimination of serum-derived impurities in the recovered virus suspension. The volume of the serum-free medium after the medium replacement may be adjusted as needed. The timing of the medium replacement is preferably 1 to 3 days, more preferably 1 to 2 days, before the day of recovering the culture supernatant.

Step (d): After culture for the predetermined period of time, the culture supernatant containing a parvovirus is recovered. As a conventional method, there is a method for recovering the virus by destroying the infected host cells by the repetition of freezing and thawing, or the like; however, here, a large amount of impurities in the host cells occur and the concentration of the impurities is relatively increased even though the virus is obtained at a high infectivity titer. As such, upon using the virus, various operations, such as ultracentrifugal purification, are required. In contrast, although impurities derived from host cells collapsed by virus infection contaminated even in the method for recovering the culture supernatant according to the present embodiment, the amount of the impurities is significantly small in the present embodiment compared to that for the destruction of host cells by freezing and thawing. Thus, according to the present embodiment, the parvovirus is obtained at a high infectivity titer from the culture supernatant and can be simply recovered.

The above method of the present embodiment can be performed to provide a parvovirus solution (including the culture supernatant and the impurity-removed virus suspension) at $10^8$ TCID$_{50}$/mL, preferably $10^{8.3}$ TCID$_{50}$/mL or more, more preferably $10^{8.5}$ TCID$_{50}$/mL or more.

The resultant parvovirus culture supernatant having an infectivity titer as high as $10^8$ TCID$_{50}$/mL or more may be subjected to low-speed centrifugation under known conditions in order to remove impurities, such as free host cells and host cell debris, and the like. Alternatively or in addition, the impurities may be removed using filtration with a membrane having a pore diameter of 0.1 to 0.5 µm, preferably 0.2 to 0.45 µm.

Further, the impurities, such as free host cells and host cell debris, may also be removed by a PEG precipitation method using known polyethylene glycol (PEG). An increase in the concentration of PEG results in the gradual precipitation of substances in descending order of molecular weight. For example, adding 10% of PEG6000 and 0.5 M of sodium chloride to 0.5 M, standing or stirring the mixture at 4 to 30° C. for 4 to 40 hours and then subjecting to centrifugation at 9,000 to 12,000 g for 20 to 60 minutes result in precipitating the parvovirus. At this time, impurity proteins are accumulated in a supernatant fraction and thus the impurities and the parvovirus can be separated for purification. Various PEGs other than PEG6000 can be used for PEG precipitation.

An anion exchange substrate can also be suitably used for the separation and purification of a parvovirus. The parvovirus has a negatively charged surface and adsorbs to the anion exchange substrate. Thus, the adsorbed parvovirus can be eluted using an elution buffer having a high salt concentration to separate the impurities from the parvovirus.

As described above, a parvovirus is cultured and recovered to provide a parvovirus solution (including a virus suspension after removing impurities) having a ratio of the infectivity titer (TCID$_{50}$/mL) of the parvovirus to the impurity protein concentration (ng/mL) of 10:1 to 5,000:1, preferably 40:1 to 3,000:1. Examples of the "impurity" include free host cells, host cell debris, and proteins derived from the host cells and serum components; however, according to the present invention, the protein concentration is used as an index showing the abundance of impurities because the free host cells and host cell debris have large sizes and can be easily removed by known methods such as the above-described centrifugation and filtration.

As described above, the present embodiment provides a parvovirus solution having an infectivity titer as high as $10^8$ TCID$_{50}$/mL or more and overcome the negative effects due to insufficient infectivity titers in using parvovirus. Three typical uses will be described below.

For the first use, or when the virus is used in research applications, such as search for antiviral agents, the presence of impurities may have adverse effects, such as inhibiting a desired reaction. Thus, a virus having a higher infectivity titer than the virus infectivity titer actually used for a test will be previously produced and used for research by dilution to an extent not affected by the impurities. To allow the measurement of high virus-inhibiting activity, the virus must be provided at a high virus infectivity titer for the test; thus, it is necessary to previously produce the virus at a higher infectivity titer than that titer. In other words, it is desirable that the virus obtained by cell culture has high infectivity titer. The present embodiment provides a parvovirus solution having an infectivity titer as high as $10^8$ TCID$_{50}$/mL or more, enabling the parvovirus to be used as a material for research after dilution in the research of antiviral drugs using the parvovirus. This enables the reduction of unexpected reactions and interference due to impurities.

For the second use, or when the virus is produced to evaluate virus clearance of the production steps of a biologics, it is also desirable that the virus has high infectivity titer. As described above, the required points for the virus clearance test are, firstly, that the addition amount of a virus suspension is an amount to an extent not clogging the holes of the filter, and secondly, that the addition amount is an amount capable of ensuring that the log reduction value (LRV) as a virus clearance value for a step to be evaluated is 4 or more. For LRV to be 4 or more, the virus must be added to an intermediate product that is subjected to a virus removal filter step, in an amount that achieves virus infectivity titer of $10^4$ TCID$_{50}$/mL; however, actually, considering the quantitative error in the virus infectivity titer and loss in the prefilter which removes aggregates of virus particles, it is necessary to add the virus to $10^5$ TCID$_{50}$/mL or more. In order to obtain $10^5$ TCID$_{50}$/mL or more by adding 0.1% by volume of virus suspension, the infectivity titer of the original virus suspension is required to be $10^8$ TCID$_{50}$/mL or more. The present embodiment provides a parvovirus solution having a suitable purity and an infectivity titer as high as $10^8$ TCID$_{50}$/mL or more, and significantly decreases the amount of parvovirus solution to be added upon evaluating the parvovirus clearance of each step. This solves the problem of clogging in a filter due to impurities derived from the parvovirus solution.

For the third use, or in vaccine production, a higher infectivity titer of the virus produced by cell culture reduces the burden in a subsequent virus vaccine purification step and is more advantageous for production. A low virus infectivity titer relatively increases the impurity concentration and makes the purification step a burdensome step, which is disadvantageous for production. Since the present embodiment provides a parvovirus solution having an infectivity titer as high as $10^8$ TCID$_{50}$/mL or more, in the production of a parvovirus vaccine, the amount of the vaccine in the starting material for purification is drastically increased, enabling the vaccine purification step to be efficiently performed with low cost.

EXAMPLES

The present invention will be described below in detail with reference to Examples and Comparative Examples. However, the Examples described here are typical examples, and the present invention is not intended to be limited to these Examples.

Example 1

PK-13 cells (purchased from ATCC) were used as host cells for porcine parvovirus (PPV) and passage cultured in DMEM medium containing 10% fetal bovine serum (hereinafter referred to as "serum medium", and the same applies to Examples described hereafter.) in an environment of 37° C. and 5% $CO_2$ using a flask for tissue culture, having a bottom area of 75 $cm^2$ and a volume of 15 mL (hereinafter referred to as "flask", and the same applies to Examples described hereafter.). The number of the host cells in the flask was measured every 24 hours and their doubling time during the log growth phase was measured. As a result, the doubling time was found to be 17 hours. The average of the numbers of cells at the day at which the highest number of the cells is reached and the days before and after that day was measured as the cell density of the host cells at confluence. As a result, the density was found to be $2.0 \times 10^7$ cells/flask.

Then, the PK-13 cells were detached from the flask, and the host cells having cell densities of 1/500 ($4.0 \times 10^4$ cells/flask), 1/200 ($1.0 \times 10^5$ cells/flask), and 1/40 ($5.0 \times 10^5$ cells/flask) of the cell density at confluence were dispensed together with 15 mL of serum medium into new flasks. The cells were dispensed into 6 flasks for each cell density conditions. PPV was then inoculated into each flask to give an MOI of 0.01 and cultured in an environment of 37° C. and 5% $CO_2$. When infection was performed in the culture vessel as described above, the seed virus infected the host cells within 2 hours and was taken up by the cells. At this time, the parvovirus once disappeared from the culture solution and entered the so-called eclipse period. At this time, some cells were in a state infected with the parvovirus. Thereafter, some cells were led to death due to the parvovirus infection, but the number of all cells was surprisingly increased.

A culture supernatant was recovered for each flask once culture had been performed for 85 hours (5 times the doubling time), 102 hours (6 times the same), 119 hours (7 times the same), 136 hours (8 times the same), 153 hours (9 times the same), and 187 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in a 96-well plate by the $TCID_{50}$ method using a method for determining infection utilizing hemagglutinin reaction. The 50% infectivity titer was calculated by the Reed-Muench method (Medical Virology, 2000, Nankodo Co., Ltd., p. 171-172). The results are shown in Table 1. Table 1 showed that the resultant virus infectivity titer was as high as $10^8$ $TCID_{50}$/mL or more. (Values in Table 1 each represent the infectivity titer as a logarithmic value. For example, 8.1 refers to $10^{8.1}$ $TCID_{50}$/mL).

In addition, the impurity protein concentration was measured using a protein assay reagent (Bradford method) from BioRad Co., Ltd. to determine the ratio of the PPV infectivity titer ($TCID_{50}$/mL) to the impurity protein concentration (ng/mL). The results are shown in Table 2.

TABLE 1

PPV Titer in Culture Supernatant after PK-13 Infection (Unit: log [$TCID_{50}$/mL])

| Culture Time after Infection | Initial Cell Density at Infection (Cells/Flask) | | |
|---|---|---|---|
| (Hour) | $4.0 \times 10^4$ | $1.0 \times 10^5$ | $5.0 \times 10^5$ |
| 85 | 8.1 | 8.7 | 8.3 |
| 102 | 8.2 | 8.7 | 8.5 |
| 119 | 8.3 | 8.7 | 8.7 |
| 136 | 8.3 | 8.7 | 8.7 |
| 153 | 8.2 | 8.0 | 8.3 |
| 187 | 8.2 | 8.0 | 8.4 |

TABLE 2

Ratio of PPV Titer (Unit: log [$TCID_{50}$/mL]) to Impurity Protein Concentration (mg/mL) in Culture Supernatant after PK-13 Infection

| Culture Time after Infection | Initial Cell Density at Infection (Cells/Flask) | | |
|---|---|---|---|
| (Hour) | $4.0 \times 10^4$ | $1.0 \times 10^5$ | $5.0 \times 10^5$ |
| 85 | 84:1 | 358:1 | 105:1 |
| 102 | 99:1 | 313:1 | 144:1 |
| 119 | 125:1 | 278:1 | 218:1 |
| 136 | 117:1 | 278:1 | 218:1 |
| 153 | 99:1 | 56:1 | 100:1 |
| 187 | 99:1 | 53:1 | 140:1 |

Comparative Example 1

When PK-13 cells were passage cultured as in Example 1 to measure the doubling time and the cell density at confluence, the doubling time was found to be 17 hours, and the cell density at confluence, $2.0 \times 10^7$ cells/flask. Then, the host cells having cell densities of 1/2,000 ($1.0 \times 10^4$ cells/flask), 1/4 ($5.0 \times 10^6$ cells/flask), 1/2.65 ($7.5 \times 10^6$ cells/flask), 1/2 ($1.0 \times 10^7$ cells/flask), and 1/1 ($2.0 \times 10^7$ cells/flask) of the cell density at confluence were dispensed together with 15 mL of serum medium into new flasks. The cells were dispensed into 6 flasks for each cell density conditions. PPV was then inoculated into each flask to give an MCI of 0.01 and cultured in an environment of 37° C. and 5% $CO_2$. A culture supernatant was recovered for each flask once culture had been performed for 85 hours (5 times the doubling time), 102 hours (6 times the same), 119 hours (7 times the same), 136 hours (8 times the same), 153 hours (9 times the same), and 187 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 3. Table 3 showed that the infectivity titer did not reach $10^8$ $TCID_{50}$/mL or more under any of the conditions.

In addition, the ratio of the PPV infectivity titer ($TCID_{50}$/mL) to the impurity protein concentration (ng/mL) was determined as in Example 1. The results are shown in Table 4.

TABLE 3

PPV Titer in Culture Supernatant after PK-13 Infection
(Unit: log [TCID$_{50}$/mL])

| Culture Time after Infection | Initial Cell Density at Infection (Cells/Flask) | | | | |
|---|---|---|---|---|---|
| (Hour) | $1.0 \times 10^4$ | $5.0 \times 10^6$ | $7.5 \times 10^6$ | $1.0 \times 10^7$ | $2.0 \times 10^7$ |
| 85  | * | 6.0 | 5.5 | 5.8 | 5.0 |
| 102 | * | 7.2 | 6.3 | 4.7 | 4.5 |
| 119 | * | 7.0 | 6.3 | 5.0 | 4.5 |
| 136 | * | 7.0 | 6.3 | 5.5 | 5.0 |
| 153 | * | 7.0 | 6.5 | 6.5 | 4.5 |
| 187 | * | 6.7 | 5.8 | 6.5 | 5.5 |

*: Cell growth was not seen because the initial number of cells was too small, and thus the experiment could not be done.

TABLE 4

Ratio of PPV Titer (Unit: log [TCID$_{50}$/mL]) to Impurity Protein Concentration (mg/mL) in Culture Supernatant after PK-13 Infection

| Culture Time after Infection | Initial Cell Density at Infection (Cells/Flask) | | | |
|---|---|---|---|---|
| (Hour) | $5.0 \times 10^6$ | $7.5 \times 10^6$ | $1.0 \times 10^7$ | $2.0 \times 10^7$ |
| 85  | 1:1  | 0.2:1 | 0.2:1  | 0.03:1 |
| 102 | 11:1 | 1:1   | 0.01:1 | 0.01:1 |
| 119 | 6:1  | 0.9:1 | 0.03:1 | 0.01:1 |
| 136 | 7:1  | 0.9:1 | 0.1:1  | 0.03:1 |
| 153 | 7:1  | 1.3:1 | 0.8:1  | 0.01:1 |
| 187 | 4:1  | 0.3:1 | 0.8:1  | 0.08:1 |

TABLE 5

PPV Titer in Culture Supernatant after PK-13 Infection
(Unit: log [TCID$_{50}$/mL])

| Culture Time after Infection | MOI | | | | | |
|---|---|---|---|---|---|---|
| (Hour) | 0.0001 | 0.001 | 0.003 | 0.01 | 0.03 | 0.1 |
| 119 | 8.3 | 8.5 | 8.5 | 8.7 | 8.3 | 8.5 |
| 136 | 8.3 | 8.5 | 8.7 | 8.7 | 8.5 | 8.3 |
| 153 | 8.3 | 8.5 | 8.5 | 8.3 | 8.4 | 8.3 |
| 187 | 8.3 | 8.3 | 8.3 | 8.4 | 8.3 | 8.2 |

TABLE 6

Ratio of PPV Titer (Unit: log [TCID$_{50}$/mL]) to Impurity Protein Concentration (mg/mL) in Culture Supernatant after PK-13 Infection

| Culture Time after Infection | MOI | | | | | |
|---|---|---|---|---|---|---|
| (Hour) | 0.0001 | 0.001 | 0.003 | 0.01 | 0.03 | 0.1 |
| 119 | 111:1 | 186:1 | 166:1 | 295:1 | 117:1 | 198:1 |
| 136 | 111:1 | 166:6 | 251:1 | 278:1 | 176:1 | 111:1 |
| 153 | 105:1 | 166:1 | 176:1 | 100:1 | 126:1 | 111:1 |
| 187 | 105:1 | 111:1 | 105:1 | 126:1 | 87:1  | 93:1  |

Example 2

When PK-13 cells were passage cultured as in Example 1 to measure the doubling time and the cell density at confluence, the doubling time was found to be 17 hours, and the cell density at confluence, $2.0 \times 10^7$ cells/flask. Then, the host cells having a cell density of 1/40 ($5.0 \times 10^5$ cells/flask) of the cell density at confluence were dispensed together with 15 mL of serum medium into new flasks. The cells were dispensed into 4 flasks for each cell density conditions. PPV was then inoculated into each flask to give an MOI of 0.0001, 0.001, 0.003, 0.01, 0.03, or 0.1 and cultured in an environment of 37° C. and 5% $CO_2$. A culture supernatant was recovered for each flask once culture had been performed for 119 hours (7 times the doubling time), 136 hours (8 times the same), 153 hours (9 times the same), and 187 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 5. Table 5 showed that the resultant virus infectivity titer was as high as $10^8$ TCID$_{50}$/mL or more for any of the MOIs.

In addition, the ratio of the PPV infectivity titer (TCID$_{50}$/mL) to the impurity protein concentration (ng/mL) was determined as in Example 1. The results are shown in Table 6.

Example 3

When PK-13 cells were passage cultured as in Example 1 to measure the doubling time and the cell density at confluence, the doubling time was found to be 17 hours, and the cell density at confluence, $2.0 \times 10^7$ cells/flask. Then, the host cells having cell densities of 1/600 ($3.4 \times 10^4$ cells/flask), 1/400 ($5.0 \times 10^4$ cells/flask), and 1/80 ($2.5 \times 10^5$ cells/flask) of the cell density at confluence were dispensed together with 15 mL of serum medium into new flasks. The cells were dispensed into 12 flasks for each cell density conditions. Subsequently, the flasks were each cultured in an environment of 37° C. and 5% $CO_2$ for 17 hours; once the number of the cells increased 2-fold, PPV was inoculated to give an MOI of 0.01 (6 flasks) or 0.003 (6 flasks) to continue the culture. A culture supernatant was recovered for each flask once culture had been performed for 85 hours (5 times the doubling time), 102 hours (6 times the same), 119 hours (7 times the same), 136 hours (8 times the same), 153 hours (9 times the same), and 187 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 7. Table 7 showed that the virus infectivity titer was as high as $10^8$ TCID$_{50}$/mL or more.

In addition, the ratio of the PPV infectivity titer (TCID$_{50}$/mL) to the impurity protein concentration (ng/mL) was determined as in Example 1. The results are shown in Table 8.

TABLE 7

PPV Titer in Culture Supernatant When PPV Was Infected 17 Hours after Planting PK-13 Cells (Unit: log [$TCID_{50}$/mL])

| Culture Time after Infection | Cell Density at Infection (Cells/Flask) | | | | | |
|---|---|---|---|---|---|---|
| | $6.7 \times 10^4$ | | $1.0 \times 10^5$ | | $5.0 \times 10^5$ | |
| | MOI | | | | | |
| (Hour) | 0.01 | 0.003 | 0.01 | 0.003 | 0.01 | 0.003 |
| 85 | 8.1 | 8.0 | 8.3 | 8.3 | 8.3 | 8.1 |
| 102 | 8.2 | 8.2 | 8.5 | 8.5 | 8.3 | 8.7 |
| 119 | 8.5 | 8.5 | 8.9 | 8.7 | 8.7 | 9.0 |
| 136 | 8.5 | 8.3 | 8.5 | 8.7 | 8.5 | 8.9 |
| 153 | 8.3 | 8.3 | 8.3 | 8.5 | 8.5 | 8.7 |
| 187 | 8.2 | 8.3 | 8.3 | 8.3 | 8.3 | 8.7 |

TABLE 8

Ratio of PPV Titer (Unit: log [$TCID_{50}$/mL]) to Impurity Protein Concentration (mg/mL) in Culture Supernatant When PPV Was Infected 17 Hours after Planting PK-13 Cells

| Culture Time after Infection | Cell Density at Infection (Cells/Flask) | | | | | |
|---|---|---|---|---|---|---|
| | $6.7 \times 10^4$ | | $1.0 \times 10^5$ | | $5.0 \times 10^5$ | |
| | MOI | | | | | |
| (Hour) | 0.01 | 0.003 | 0.01 | 0.003 | 0.01 | 0.003 |
| 85 | 74:1 | 59:1 | 117:1 | 125:1 | 111:1 | 70:1 |
| 102 | 88:1 | 88:1 | 166:1 | 166:1 | 105:1 | 251:1 |
| 119 | 166:1 | 176:1 | 418:1 | 251:1 | 251:1 | 500:1 |
| 136 | 176:1 | 105:1 | 166:1 | 251:1 | 166:1 | 441:1 |
| 153 | 111:1 | 111:1 | 117:1 | 176:1 | 158:1 | 251:1 |
| 187 | 88:1 | 111:1 | 111:1 | 111:1 | 111:1 | 278:1 |

Example 4

When PK-13 cells were passage cultured as in Example 1 to measure the doubling time and the cell density at confluence, the doubling time was found to be 17 hours, and the cell density at confluence was found to be $2.0\times10^7$ cells/flask. Then, the host cells having cell densities of 1/80 ($2.5\times10^5$ cells/flask) and 1/60 ($3.4\times10^5$ cells/flask) of the cell density at confluence were dispensed together with 15 mL of serum medium into new flasks. The cells were dispensed into 2 flasks for each cell density conditions. Culture was then performed in an environment of 37° C. and 5% $CO_2$ for 17 hours; once the number of the cells increased 2-fold, PPV was inoculated to give an MCI of 0.01 to continue the culture. The culture supernatant was removed 4 days (96 hours) after the start of infection; the cells on the bottom face of the flask were washed with DMEM medium containing no serum (hereinafter referred to as "serum-free medium"), followed by adding 10 mL of the serum-free medium and further performing culture; and about 1 day later (119 hours after the start of infection=7 times the doubling time) or 2 days later (136 hours after the start of infection=8 times the same), the culture supernatant of the serum-free medium was recovered for each flask. The recovered serum-free culture supernatant was centrifuged at 3,000 rpm for 20 minutes, and the supernatant fraction was filtered using a 0.45-μm filter (from Nalgene).

The serum-free PPV infectivity titer was measured in the same way as in Example 1 using a 96-well plate. The results are shown in Table 9. Table 9 showed that the virus infectivity titer was as high as $10^8$ $TCID_{50}$/mL or more under any of the conditions.

In addition, the ratio of the PPV infectivity titer ($TCID_{50}$/mL) to the impurity protein concentration (ng/mL) was determined as in Example 1. The results are shown in Table 10.

TABLE 9

PPV Titer in Culture Supernatant When PPV Was Infected 17 Hours after Planting PK-13 Cells and Serum Medium Was Replaced with Serum-free Medium during Culture (Unit: log [$TCID_{50}$/mL])

| Culture Time after Infection | Cell Density at Infection (Cells/Flask) | |
|---|---|---|
| (Hour) | $5.0 \times 10^5$ | $6.7 \times 10^5$ |
| 119 | 8.3 | 8.5 |
| 136 | 8.7 | 8.5 |

TABLE 10

Ratio of PPV Titer (Unit: log [$TCID_{50}$/mL]) to Impurity Protein Concentration (mg/mL) in Culture Supernatant When PPV Was Infected 17 Hours after Planting PK-13 Cells and Serum Medium Was Replaced with Serum-free Medium during Culture

| Culture Time after Infection | Cell Density at Infection (Cells/Flask) | |
|---|---|---|
| (Hour) | $5.0 \times 10^5$ | $6.7 \times 10^5$ |
| 119 | 998:1 | 1054:1 |
| 136 | 2506:1 | 1581:1 |

Example 5

Passage culture was performed under the same culture conditions as those in Example 1 except for using ESK cells (Vet. Microbiol. 1984, 9(2): 187-92, Microbiologica 1987, 10(3): 301-9, Nippon Juigaku Zasshi 1988, 50(3): 803-8, Nippon Juigaku Zasshi. 1990, 52(2): 217-24, J. Vet. Med. Sci. 1992, 54(2): 313-8) as a porcine kidney-derived cell line widely used as host cells for porcine parvovirus (PPV), in place of PK-13 cells. When the doubling time and the cell density at confluence were measured, they were found to be 20 hours and $3.0\times10^7$ cells/flask, respectively.

The ESK cells were detached from the flask, and the host cells having cell densities of 1/500 ($6.0\times10^4$ cells/flask), 1/300 ($1.0\times10^5$ cells/flask), 1/200 ($1.5\times10^5$ cells/flask), 1/40 ($7.5\times10^5$ cells/flask), 1/30 ($1.0\times10^6$ cells/flask), and 1/20 ($1.5\times10^6$ cells/flask) of the cell density at confluence were dispensed together with 15 mL of serum medium into new flasks. The cells were dispensed into 6 flasks for each cell density conditions. PPV was then inoculated into each flask to give an MOI of 0.01 and cultured under the same culture conditions as those in Example 1. A culture supernatant was recovered for each flask once culture had been performed for 100 hours (5 times the doubling time), 120 hours (6 times the same), 140 hours (7 times the same), 160 hours (8 times the same), 180 hours (9 times the same), and 220 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1. The results are shown in Table 11. Table 11 showed that the virus infectivity titer was as high as $10^8$ $TCID_{50}$/mL or more for any of the conditions.

In addition, the ratio of the PPV infectivity titer ($TCID_{50}$/mL) to the impurity protein concentration (ng/mL) was determined as in Example 1. The results are shown in Table 12.

TABLE 11

PPV Titer in Culture Supernatant after Infection with ESK Cell (Unit: log [$TCID_{50}$/mL])

| Culture Time after Infection (Hour) | Initial Cell Density at Infection (Cells/Flask) | | | | | |
|---|---|---|---|---|---|---|
| | $6.0 \times 10^4$ | $1.0 \times 10^5$ | $1.5 \times 10^5$ | $7.5 \times 10^5$ | $1.0 \times 10^6$ | $1.5 \times 10^6$ |
| 100 | 8.2 | 8.3 | 8.3 | 8.3 | 8.2 | 8.1 |
| 120 | 8.2 | 8.3 | 8.7 | 8.5 | 8.2 | 8.3 |
| 140 | 8.2 | 8.7 | 8.7 | 8.7 | 8.3 | 8.3 |
| 160 | 8.2 | 8.5 | 8.5 | 8.7 | 8.3 | 8.3 |
| 180 | 8.1 | 8.2 | 8.3 | 8.5 | 8.3 | 8.2 |
| 220 | 8.1 | 8.2 | 8.1 | 8.3 | 8.1 | 8.2 |

TABLE 12

Ratio of PPV Titer (Unit: log [$TCID_{50}$/mL]) to Impurity Protein Concentration (mg/mL) in Culture Supernatant after Infection with ESK Cell

| Culture Time after Infection (Hour) | Initial Cell Density at Infection (Cells/Flask) | | | | | |
|---|---|---|---|---|---|---|
| | $6.0 \times 10^4$ | $1.0 \times 10^5$ | $1.5 \times 10^5$ | $7.5 \times 10^5$ | $1.0 \times 10^6$ | $1.5 \times 10^6$ |
| 100 | 79:1 | 100:1 | 100:1 | 91:1 | 88:1 | 63:1 |
| 120 | 75:1 | 91:1 | 218:1 | 137:1 | 83:1 | 100:1 |
| 140 | 72:1 | 251:1 | 209:1 | 218:1 | 100:1 | 91:1 |
| 160 | 69:1 | 137:1 | 122:1 | 228:1 | 83:1 | 95:1 |
| 180 | 55:1 | 69:1 | 74:1 | 137:1 | 77:1 | 66:1 |
| 220 | 57:1 | 63:1 | 48:1 | 91:1 | 52:1 | 72:1 |

Comparative Example 2

When PK-13 cells were passage cultured as in Example 1 to measure the doubling time and the cell density at confluence, the doubling time was found to be 17 hours, and the cell density at confluence, $2.0 \times 10^7$ cells/flask. Then, the host cells having cell densities of 1/40 ($5 \times 10^5$ cells/flask) of the cell density at confluence were dispensed together with 15 mL of serum medium into new flasks. The cells were dispensed into 4 flasks for each cell density conditions. PPV was then inoculated into each flask to give an MOI of 0.0001, 0.001, 0.003, 0.01, 0.03, or 0.1 and cultured in an environment of 37° C. and 5% $CO_2$. A culture supernatant was recovered for each flask once culture had been performed for 51 hours (3 times the doubling time), 68 hours (4 times the same), 204 hours (12 times the same), and 238 hours (14 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 13. Table 13 showed that the infectivity titer did not reach $10^8$ $TCID_{50}$/mL or more under any of the conditions.

In addition, the ratio of the PPV infectivity titer ($TCID_{50}$/mL) to the impurity protein concentration (ng/mL) was determined as in Example 1. The results are shown in Table 14.

TABLE 13

PPV Titer in Culture Supernatant after PK-13 Infection (Unit: log [$TCID_{50}$/mL])

| Culture Time after Infection (Hour) | MOI | | | | | |
|---|---|---|---|---|---|---|
| | 0.0001 | 0.001 | 0.003 | 0.01 | 0.03 | 0.1 |
| 51 | 2.7 | 4.5 | 5.3 | 5.5 | 4.7 | 4.5 |
| 68 | 4.5 | 5.5 | 6.5 | 6.7 | 6.0 | 5.5 |
| 204 | 7.5 | 7.5 | 7.5 | 7.5 | 7.3 | 7.3 |
| 238 | 6.5 | 6.7 | 6.7 | 7.0 | 6.2 | 5.7 |

TABLE 14

Ratio of PPV Titer (Unit: log [$TCID_{50}$/mL]) to Impurity Protein Concentration (mg/mL) in Culture Supernatant after PK-13 Infection

| Culture Time after Infection (Hour) | MOI | | | | | |
|---|---|---|---|---|---|---|
| | 0.0001 | 0.001 | 0.003 | 0.01 | 0.03 | 0.1 |
| 51 | 0.0003:1 | 0.02:1 | 0.1:1 | 0.2:1 | 0.03:1 | 0.02:1 |
| 68 | 0.02:1 | 0.2:1 | 1.9:1 | 3:1 | 0.6:1 | 0.2:1 |

TABLE 14-continued

Ratio of PPV Titer (Unit: log [TCID$_{50}$/mL]) to Impurity Protein Concentration (mg/mL) in Culture Supernatant after PK-13 Infection

| Culture Time after Infection (Hour) | MOI | | | | | |
|---|---|---|---|---|---|---|
| | 0.0001 | 0.001 | 0.003 | 0.01 | 0.03 | 0.1 |
| 204 | 13:1 | 12:1 | 16:1 | 16:1 | 10:1 | 9:1 |
| 238 | 1:1 | 2:1 | 2:1 | 5:1 | 0.7:1 | 0.2:1 |

Comparative Example 3

When PK-13 cells were passage cultured as in Example 1 to measure the doubling time and the cell density at confluence, the doubling time was found to be 17 hours, and the cell density at confluence, 2.0×10$^7$ cells/flask. Then, the host cells having cell densities of 1/40 (5.0×10$^5$ cells/flask) of the cell density at confluence were dispensed together with 15 mL of serum medium into new flasks. The cells were dispensed into 6 flasks for each cell density conditions. PPV was then inoculated into each flask to give an MOI of 0.00001 or 1.0 and cultured in an environment of 37° C. and 5% CO$_2$. A culture supernatant was recovered for each flask once culture had been performed for 85 hours (5 times the doubling time), 102 hours (6 times the same), 119 hours (7 times the same), 136 hours (8 times the same), 153 hours (9 times the same), and 187 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 15. Table 15 showed that the infectivity titer did not reach 10$^8$ TCID$_{50}$/mL or more under any of the conditions.

In addition, the ratio of the PPV infectivity titer (TCID$_{50}$/mL) to the impurity protein concentration (ng/mL) was determined as in Example 1. The results are shown in Table 16.

TABLE 15

PPV Titer in Culture Supernatant after PK-13 Infection (Unit: log [TCID$_{50}$/mL])

| Culture Time after Infection (Hour) | MOI | |
|---|---|---|
| | 0.00001 | 1.0 |
| 85 | 2.0 | 4.5 |
| 102 | 2.3 | 5.0 |
| 119 | 3.0 | 5.3 |
| 136 | 3.5 | 5.0 |
| 153 | 4.0 | 4.7 |
| 187 | 4.4 | 4.5 |

TABLE 16

Ratio of PPV Titer (Unit: log [TCID$_{50}$/mL]) to Impurity Protein Concentration (mg/mL) in Culture Supernatant after PK-13 Infection

| Culture Time after Infection (Hour) | MOI | |
|---|---|---|
| | 0.00001 | 1.0 |
| 85 | 0.0001:1 | 0.00001:1 |
| 102 | 0.0001:1 | 0.01:1 |
| 119 | 0.0005:1 | 0.05:1 |
| 136 | 0.002:1 | 0.09:1 |
| 153 | 0.005:1 | 0.04:1 |
| 187 | 0.01:1 | 0.02:2 |

Comparative Example 4

When ESK cells were passage cultured as in Example 5 to measure the doubling time and the cell density at confluence, the doubling time was found to be 20 hours, and the cell density at confluence, 3.0×10$^7$ cells/flask. Then, the host cells having cell densities of 1/2,000 (1.5×10$^4$ cells/flask), 1/4 (7.5×10$^6$ cells/flask), 1/2.65 (1.1×10$^7$ cells/flask), 1/2 (1.5×10$^7$ cells/flask), and 1/1 (3.0×10$^7$ cells/flask) of the cell density at confluence were dispensed together with 15 mL of serum medium into new flasks. The cells were dispensed into 6 flasks for each cell density conditions. PPV was then inoculated into each flask to give an MCI of 0.01 and cultured as in Example 5. A culture supernatant was recovered for each flask once culture had been performed for 100 hours (5 times the doubling time), 120 hours (6 times the same), 140 hours (7 times the same), 160 hours (8 times the same), 180 hours (9 times the same), and 220 hours (11 times the same) after starting infection. The recovered culture supernatant was centrifuged at 3,000 rpm for 20 minutes, and the supernatant fraction was filtered using a 0.45-μm filter (from Nalgene).

The PPV infectivity titer was measured in the same way as in Example 1 using a 96-well plate. The results are shown in Table 17. Table 17 showed that the infectivity titer did not reach 10$^8$ TCID$_{50}$/mL or more under any of the conditions.

In addition, the ratio of the PPV infectivity titer (TCID$_{50}$/mL) to the impurity protein concentration (ng/mL) was determined as in Example 1. The results are shown in Table 18.

TABLE 17

PPV Titer in Culture Supernatant after PPV Growth Using ESK Cell (Unit: log [TCID$_{50}$/mL])

| Culture Time after Infection (Hour) | Initial Cell Density at Infection (Cells/Flask) | | | | |
|---|---|---|---|---|---|
| | 1.5 × 10$^4$ | 7.5 × 10$^6$ | 1.1 × 10$^7$ | 1.5 × 10$^7$ | 3.0 × 10$^7$ |
| 100 | * | 5.7 | 5.7 | 6.1 | 5.2 |
| 120 | * | 6.0 | 6.3 | 5.7 | 4.6 |
| 140 | * | 6.7 | 6.3 | 6.0 | 5.0 |
| 160 | * | 7.0 | 6.5 | 6.3 | 4.7 |
| 180 | * | 7.0 | 6.3 | 6.0 | 4.7 |
| 220 | * | 6.7 | 6.0 | 5.7 | 5.0 |

*: Cell growth was not seen because the initial number of cells was too low, and thus the experiment could not be done.

TABLE 18

| Ratio of PPV Titer (Unit: log [$TCID_{50}$/mL]) to Impurity Protein Concentration (mg/mL) in Culture Supernatant after PPV Growth Using ESK Cell | | | | |
|---|---|---|---|---|
| Culture Time after Infection | Initial Cell Density at Infection (Cells/Flask) | | | |
| (Hour) | $7.5 \times 10^6$ | $1.1 \times 10^7$ | $1.5 \times 10^7$ | $3 \times 10^7$ |
| 100 | 0.3:1 | 0.3:1 | 0.7:1 | 0.1:1 |
| 120 | 0.6:1 | 1:1 | 0.3:1 | 0.02:1 |
| 140 | 3:1 | 1:1 | 0.4:1 | 0.04:1 |
| 160 | 6:1 | 2:1 | 0.8:1 | 0.02:1 |
| 180 | 6:1 | 0.9:1 | 0.4:1 | 0.02:1 |
| 220 | 3:1 | 0.5:1 | 0.2:1 | 0.05:1 |

INDUSTRIAL APPLICABILITY

According to the method of the present invention, a parvovirus solution having a suitable purity and an infectivity titer as high as $10^8$ $TCID_{50}$/mL or more is obtained. This can be used for the preparation of a virus research material for searching antiviral agents, the preparation of a virus used for virus clearance safety evaluation in a biologics (pharmaceutical product) production steps, vaccine production, and the like.

This application claims priority to Japanese Patent Application No. 2012-256801, filed on Nov. 22, 2012, the contents of which are incorporated herein by reference.

The invention claimed is:

1. A method for producing a parvovirus in a culture supernatant by culturing host cells and a seed virus of the parvovirus in a culture substrate, comprising:

(a) calculating: a doubling time of the host cells during the log growth phase in the culturing; and a cell density of the host cells confluently grown in the culturing;

(b) inoculating the seed virus of the parvovirus into the culture substrate comprising a medium and the host cells having a cell density of 1/500 to 1/20 of the cell density of the host cells confluently grown, calculated in (a), to give a multiplicity of infection (MOI) of 0.0001 to 0.1;

(c) culturing the culture comprising the medium and the host cells having a cell density of 1/500 to 1/20 of the cell density of the host cells confluently grown and the inoculated parvovirus obtained in (b) for a period of 5 to 11 times the doubling time calculated in (a); and (d) recovering a culture supernatant comprising the parvovirus, obtained by the culturing (c).

2. The method according to claim 1, wherein the host cell is an adhesion-dependent cell.

3. The method according to claim 1, wherein the host cell is a cell susceptible to the parvovirus.

4. The method according to claim 1, wherein the parvovirus is porcine parvovirus (PPV), canine parvovirus (CPV), minute virus of mice (MVM), rat virus (RV), H-1 virus (H-1), feline parvovirus (FPV), goose parvovirus (GPV), or bovine parvovirus (BPV).

5. The method according to claim 1, wherein in (b), the seed virus of the parvovirus is inoculated into the culture substrate comprising a medium and the host cells having a cell density of 1/300 to 1/30 of the cell density of the host cells confluently grown, calculated in (a), to give a multiplicity of infection (MOI) of 0.0001 to 0.1.

6. The method according to claim 1, wherein in (b), the seed virus of the parvovirus is inoculated into the culture substrate comprising a medium and the host cells having a cell density of 1/200 to 1/40 of the cell density of the host cells confluently grown, calculated in (a), to give a multiplicity of infection (MOI) of 0.0001 to 0.1.

7. The method according to claim 1, wherein the multiplicity of infection (MOI) is 0.001 to 0.03.

8. The method according to claim 7, wherein the multiplicity of infection (MOI) is 0.003 to 0.01.

9. The method according to claim 1, wherein when the medium is a serum medium, (c) comprises replacing the serum medium with a serum-free medium.

10. The method for producing a parvovirus according to claim 1, wherein in (c), the culture is cultured for a period of 6 to 9 times the doubling time calculated in (a).

11. The method for producing a parvovirus according to claim 10, wherein in (c), the culture is cultured for a period of 7 to 8 times the doubling time calculated in (a).

12. The method for producing a parvovirus according to claim 1, wherein in (c), the culture is cultured at a temperature of from 33° C. to 39° C.

13. The method for producing a parvovirus according to claim 1, wherein in (c), the host cells and the virus grow concurrently.

14. The method according to claim 1, wherein (d) comprises removing free host cells and host cell debris contained in the culture supernatant.

15. The method according to claim 14, wherein the removing is performed using filtration with a membrane having a pore diameter of 0.2 μm to 0.45 μm.

* * * * *

UNITED STATES PATENT AND TRADEMARK OFFICE
CERTIFICATE OF CORRECTION

| | |
|---|---|
| PATENT NO. | : 9,809,800 B2 |
| APPLICATION NO. | : 14/646115 |
| DATED | : November 7, 2017 |
| INVENTOR(S) | : K. Yanagida |

Page 1 of 1

It is certified that error appears in the above-identified patent and that said Letters Patent is hereby corrected as shown below:

In the Claims

Column 25, Line 31 (Claim 1, Line 1) please change "producing a parvovirus" to -- producing parvovirus --

Signed and Sealed this
Fifth Day of June, 2018

Andrei Iancu
*Director of the United States Patent and Trademark Office*